US006391319B1

United States Patent
Kröpke et al.

(12) United States Patent
(10) Patent No.: US 6,391,319 B1
(45) Date of Patent: May 21, 2002

(54) COSMETIC AND DERMATOLOGICAL EMULSIONS COMPRISING ALKYL GLUCOSIDES AND INCREASED ELECTROLYTE CONCENTRATIONS

(75) Inventors: Rainer Kröpke; Anja Lührs, both of Hamburg; Anja Müller, Rümpel; Jens Nielsen, Henstedt-Ulzburg; Andrea Bungard; Burghard Grüning, both of Essen; Klaus Jenni, Witten, all of (DE)

(73) Assignees: Beiersdorf AG, Hamburg; Th. Goldschmidt AG, Essen, both of (DE)

( * ) Notice: Subject to any disclaimer, the term of this patent is extended or adjusted under 35 U.S.C. 154(b) by 0 days.

(21) Appl. No.: 09/088,885

(22) Filed: Jun. 2, 1998

(30) Foreign Application Priority Data

Jun. 6, 1997 (DE) .......................... 197 23 733

(51) Int. Cl.[7] .......................... A61K 9/107; A61K 7/48; A61K 47/36
(52) U.S. Cl. .................. 424/401; 514/844; 514/938; 514/975; 510/72
(58) Field of Search .................. 424/401; 514/844, 514/53, 938, 943, 975; 510/72

(56) References Cited

U.S. PATENT DOCUMENTS

| 5,100,573 A | 3/1992 | Balzer |
| 5,494,938 A | 2/1996 | Kawa et al. |
| 5,510,100 A | 4/1996 | Picard et al. .................. 424/59 |
| 5,605,651 A | 2/1997 | Balzer |
| 5,639,797 A | 6/1997 | Kropke et al. |
| 5,811,386 A | 9/1998 | Mueller et al. |
| 5,817,254 A | 10/1998 | Wadle et al. |

FOREIGN PATENT DOCUMENTS

| DE | 41 10 506 | 10/1992 |
| DE | 41 26 969 | 2/1993 |
| DE | 42 30 504 | 3/1994 |

(List continued on next page.)

OTHER PUBLICATIONS

English Abstract of E.P. 750,034, Dec. 27, 1996.
English Abstract of DE 195 46 416, Jun. 19, 1997.
English Abstract of DE 195 47 986, Jul. 10, 1997.
English Abstract of DE 41 26 969, Feb. 18, 1993.
English Abstract of DE 42 35 647, Apr. 28, 1994.
English Abstract of DE 42 39 679, Jun. 1, 1994.

Primary Examiner—Edward J. Webman
(74) Attorney, Agent, or Firm—Norris McLaughlin & Marcus (57) ABSTRACT

Cosmetic and dermatological emulsions having at least one aqueous phase, comprising (a) an effective amount of one or more interface-active substances, selected from the group consisting of alkyl glucosides, which are characterized by the structural formula $$\left[ \begin{array}{c} \text{structure with OH, H}_2\text{C, HO groups} \end{array} \right]_{\overline{DP}-1} \text{O---R}$$

in which R is a branched or unbranched alkyl radical having from 4 to 24 carbon atoms, (b) where in at least one of the aqueous phases one or more electrolytes is present in dissolved form, the ionic strength of the aqueous phases in which the electrolyte(s) is/are present in dissolved form being at least 0.075 mol/l,

(c) and where $\overline{DP}$ is an average degree of glucosylation of up to 2.

23 Claims, 1 Drawing Sheet

FOREIGN PATENT DOCUMENTS

| | | |
|---|---|---|
| DE | 42 35 647 | 4/1994 |
| DE | 42 39 679 | 6/1994 |
| DE | 43 02 315 | 8/1994 |
| DE | 43 35 045 | 4/1995 |
| DE | 195 03 423 | 8/1996 |
| DE | 195 46 416 | 6/1997 |
| DE | 195 47 986 | 7/1997 |
| EP | 384983 | 9/1990 |
| EP | 388810 | 9/1990 |
| EP | 408965 | 1/1991 |
| EP | 0 629 396 | 12/1994 |
| EP | 750034 | 12/1996 |
| GB | 2128627 | 5/1984 |

Fig. 1

COSMETIC AND DERMATOLOGICAL EMULSIONS COMPRISING ALKYL GLUCOSIDES AND INCREASED ELECTROLYTE CONCENTRATIONS

The present invention relates to cosmetic and dermatological emulsions, in particular skin care cosmetic and dermatological emulsions. In an advantageous embodiment, the present invention relates to a use which permits the stability of emulsions, in particular of O/W emulsions to be increased.

The outermost layer of the epidermis, the Stratum corneum (horny layer), is an important barrier layer and therefore of particular significance inter alia for protecting against environmental influences and drying out. As a result of contact with the environment, the horny layer is continually worn away and must therefore be continuously renewed.

A model for the skin which is widely used today in the expert field depicts the Stratum corneum as a two-component system, similar to a brick wall (bricks and mortar model). In this model, the corneocytes (horn cells) are the bricks and the complex lipid membrane in the intercellular spaces is the mortar.

Apart from its barrier effect against external chemical and physical influences, the epidermal lipids also contribute to the holding together of the horny layer and influence the skin smoothness. In contrast to sebaceous gland lipids, which do not form a continuous film on the skin, the epidermal lipids are distributed over the entire horny layer.

The extremely complex interaction of the moisture-binding substances and of the lipids in the upper layers of the skin is very important for regulation of skin moisture. Cosmetics thus usually comprise water-binding substances in addition to balanced lipid mixtures and water.

As well as the chemical composition, the physical behaviour of these substances is, however, also of importance. The development of highly biocompatible emulsifiers and surfactants having liquid-crystalline properties is thus desirable. Products formulated therewith support the liquid-crystalline organization of the intercellular lipids of the Stratum corneum and thus improve the barrier properties of the horny layer. It is particularly advantageous if the molecular constituents of such products consist of substances which are naturally occuring in the epidermis.

The main role of cosmetic skin care is taken to be the strengthening or restoration of the skin's natural function as a barrier against environmental influences (e.g. dirt, chemicals, microorganisms) and against the loss of endogenous substances (e.g. water, natural fats, electrolytes).

If this function is disturbed, it can lead to increased resorption of toxic or allergenic substances or to attack by microorganisms and, consequently, to toxic or allergic skin reactions.

Another aim of skin care is to replenish the fats and water lost from the skin as a result of daily washing. This is particularly important when the natural regeneration ability is inadequate. In addition, skincare products should protect against environmental influences, in particular against sun and wind, and delay skin ageing.

Medical topical compositions normally comprise one or more medicaments in an effective concentration. For the sake of simplicity, reference is made to the legal provisions of the Federal Republic of Germany (e.g. Cosmetics Regulation, Foods and Drugs Act) for a clear distinction between cosmetic and medical use and corresponding products.

Customary forms in which cosmetics are applied are emulsions, i.e. metastable two- or multi-phase systems in which the individual phases are present in the liquid state. The most common emulsions are O/W and W/O emulsions. Less common application forms are multiple emulsions, i.e. those which in the droplets of the dispersed (or discontinuous) phase for their part comprise droplets of a further dispersed phase, e.g. W/O/W emulsions and O/W/O emulsions.

In order to be able to ensure the metastability of emulsions, interface-active substances, i.e. emulsifiers, are generally necessary.

The use per se of customary cosmetic emulsifiers is completely acceptable. Nevertheless, emulsifiers, as any chemical substance, may in certain cases cause allergic reactions or reactions based on oversensitivity of the user.

For example, it is known that in some people having particularly sensitive skin certain light dermatoses are triggered by certain emulsifiers and the simultaneous action of sunlight.

It is possible to prepare emulsifier-free preparations which have, for example, in an aqueous phase, dispersed oil droplets, similar to an O/W emulsion. A prerequisite for this may be that the continuous aqueous phase has a gel backbone which stabilizes the dispersed phase and other conditions besides. Such systems are sometimes called hydrodispersions or oleodispersions depending on which is the disperse phase and which is the continuous phase.

For cosmetic technology, it is how ever neither necessary no r possible to dispense with emulsifiers altogether, especially since there is a certain choice of particularly mild emulsifiers. However, the prior art lacks a satisfactorily broad range of such emulsifiers which would then also significantly broaden the application spectrum of correspondingly mild cosmetic preparations which are tolerated by the skin.

An object of the present invention was thus to provide cosmetic and dermatological p reparations having excellent skin care properties.

A disadvantage in particular of O/W emulsions is frequently their inadequate stability to relatively high electrolyte concentrations, which manifests itself in phase separation. This can occasionally lead to problems, even in the case of W/O emulsions, although it is by no means as important here as in the case of O/W systems. Whilst these can often be remedied to a certain extent through appropriate choice of the emulsifier system, other disadvantages, however, arise just as often.

On the other hand, it is often desirable to use certain electrolytes in order to be able to utilize their other physical, chemical or physiological properties.

The concentrations of all the constituents of a cosmetic or dermatological preparation are usually given in units such as % by weight, mol-% and the like. In view of their dissociation into cations and anions, which takes place to a greater or lesser extent, often in several dissociation stages, it appears more advantageous for the description of the present invention and its technical background, to start from the ionic strength of a given electrolyte in its solution. The ionic strength I of an electrolyte solution is defined as $$I = \frac{1}{2}\sum_i c_i z_i^2$$

in which $c_i$ is the concentrations of the individual types of ion (in mol/l) and $z_i$ are their charges. The physical unit of ionic strength is that of a concentration (mol/l).

For example, a 1% strength (=0.17 molar) sodium chloride solution has an ionic strength I=0.17.

Another object of the present invention was thus to discover ways of producing cosmetic or dermatological emulsions, in particular O/W emulsions, which are stable to increased electrolyte concentrations—or increased ionic strength.

It was also an object of the present invention to provide preparations which significantly improve the condition of the skin, in particular skin roughness.

Surprisingly, it has been shown, and this is where the solution to these problems lies, that cosmetic and dermatological emulsions having at least one aqueous phase, comprising (a) an effective amount of one or more interface-active substances, selected from the group consisting of alkyl glucosides, which are characterized by the structural formula in which R is a branched or unbranched alkyl radical having from 4 to 24 carbon atoms, (b) where in at least one of the aqueous phases one or more electrolytes is present in dissolved form, the ionic strength of the aqueous phases in which the electrolyte(s) is/are present in dissolved form being at least 0.075 mol/l, (c) and where $\overline{DP}$ is an average degree of glucosylation of up to 2, remedy the prior art disadvantages.

It was thus not foreseeable by the person skilled in the art that the preparations according to the invention would be more effective moisture-donating preparations, better promote skin smoothing, be characterized by better care action, be better vehicles for cosmetic and medical-dermatological active substances have higher stability to decomposition in oil and water phases and be characterized by better biocompatibility than prior art preparations.

EP-A-0 629 396 indeed describes stable cosmetic emulsions which are characterized by a content of alkyl glucosides. According to claim 6 loc. cit., the preparations can also contain salts. The ionic strengths of the electrolytes stated therein, which are specifically disclosed in the examples and based on the weight concentrations, are 0.046 mol/l (for sodium hydroxide in Example 1), 0.023 moll (for sodium hydroxide in Example 2) and 0.03 mol/l (for Na$_2$H$_2$EDTA in Example 5) and thus much too low, to suggest the teaching according to the invention.

In EP-A-0 629 396, Example 6, yet another stable cosmetic emulsion containing an electrolyte having an ionic strength of 0.023 mol/l (for sodium hydroxide) is given, this Example 6 referring to preparations likewise having a content of alkyl glucosides, but according to WO 92/06778. The latter specification does not mention the use of electrolytes at all. Consequently, the prior art could not pave the way to the present invention.

The invention also relates to the use of cosmetic and dermatological emulsions, in particular O/W emulsions having at least one aqueous phase, comprising (a) an effective amount of one or more interface-active substances, selected from the group consisting of alkyl glucosides, which are characterized by the structural formula in which R is a branched or unbranched alkyl radical having from 4 to 24 carbon atoms, (b) where in at least one of the aqueous phases one or more electrolytes is present in dissolved form, the ionic strength of the aqueous phases in which the electrolytes) is/are present in dissolved form being at least 0.075 mol/l, (c) and where $\overline{DP}$ is an average degree of glucosylation of up to 2, for skin care.

The invention also further relates to the use of one or more interface-active substances, selected from the group consisting of alkyl glucosides which are characterized by the structural formula in which R is a branched or unbranched alkyl radical having from 4 to 24 carbon atoms, and where $\overline{DP}$ is an average degree of glucosylation of up to 2, for achieving or increasing the stability of emulsions to the presence of electrolytes, in particular for achieving or increasing the stability of O/W emulsions to the presence of electrolytes.

The invention relates in particular to the use of one or more interface-active substances, selected from the group consisting of alkyl glucosides which are characterized by the structural formula in which R is a branched or unbranched alkyl radical having from 4 to 24 carbon atoms, and where $\overline{DP}$ is an average degree of glucosylation of up to 2, for achieving or increasing the stability of emulsions to the presence of electrolytes, in particular for achieving or increasing the stability of O/W emulsions to the presence of electrolytes, in which case the emulsions, in at least one of the aqueous phases, contain one or more electrolytes in dissolved form, and the ionic strength of the aqueous phases in which the electrolyte(s) is/are present in dissolved form is at least 0.075 mol/l.

Figure 1:
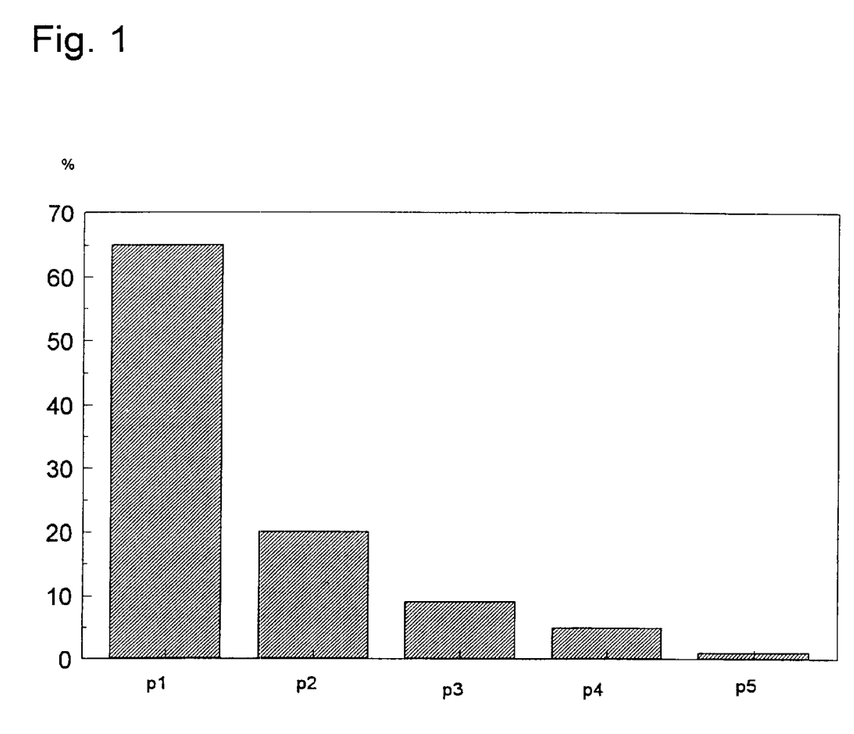

The $\overline{DP}$ value represents the degree of glucosylation of the alkyl glucosides used according to the invention and is defined as $$\overline{DP} = \frac{p_1}{100} \cdot 1 + \frac{p_2}{100} \cdot 2 + \frac{p_3}{100} \cdot 3 + \cdots = \sum_i \frac{p_i}{100} \cdot i$$

$p_1, p_2, p_3 \ldots$ and $p_i$ represent the proportion of the products glucosylated once, twice, three times . . . i times in percentages by weight. According to the invention, products with degrees of glucosylation of 1–2 are advantageous, those with degrees of from 1.1 to 1.5 are particularly advantageous and those having a degree of glucosylation of about 1.3 are very particularly advantageous.

The $\overline{DP}$ value takes into account the fact that alkyl glucosides are usually mixtures of mono- and oligoglucosides, depending on the preparation. According to the invention, a relatively high content of monoglucosides, typically in the order of magnitude of 40–70% by weight, is advantageous.

BRIEF DESCRIPTION OF THE DRAWING

A typical oligomer distribution for a degree of glucosylation of about 1.3 is shown in FIG. 1.

R is advantageously chosen from the group consisting of unbranched alkyl radicals, in which case the myristyl, cetyl, stearyl and eicosyl radicals are preferred.

Alkyl glucosides used according to the invention are obtainable by processes as described, for example, in DE-OS 40 40 655 and other specifications. They are available commercially from a variety of manufacturers.

For example, it is advantageous to use mixtures of stearyl glucoside and cetyl glucoside. Such mixtures are available commercially, for example, under the tradename Tego® Care SG 90 from Th.Goldschmidt KG.

The total amount of one or more interface-active glucose derivatives used according to the invention in the finished cosmetic or dermatological preparations is advantageously chosen from the range 0.1–25.0% by weight, preferably from 0.5–15.0% by weight, based on the total weight of the preparations.

According to the invention, the electrolyte(s) is/are advantageously chosen from the group consisting of

(1) salts containing the following anions: chlorides, also inorganic oxo-element anions, particularly sulfates, carbonates, phosphates, borates and aluminates. Electrolytes based on organic anions are also advantageous, e.g. lactates, acetates, benzoates, propionates, tartrates, citrates, amino acids and salts thereof and others besides. Comparable effects can also be achieved using ethylenediaminetetraacetic acid and salts thereof.

Cations of salts which are preferably used are ammonium, alkylammonium, alkali metal, alkaline earth metal, magnesium, iron and zinc ions. It goes without saying that in cosmetics only physiologically acceptable electrolytes should be used. Particular preference is given to potassium chloride, sodium chloride, magnesium sulphate, zinc sulphate and mixtures thereof.

According to the invention, the electrolyte(s) is/are also advantageously chosen from the group consisting of (2) Certain water-soluble UV filter substances, which are mostly present as alkali metal salts, in particular those which carry on their molecule backbone one or more sulphonic acid groups or sulphonate groups:

2-Phenylbenzimidazole-5-sulphonic acid and salts thereof, for example the sodium, potassium or its triethanolammonium salt sulphonic acid derivatives of benzophenones, preferably 2-hydroxy-4-methoxybenzophenone-5-sulphonic acid and salts thereof, for example the corresponding sodium, potassium or triethanolammonium salt:

sulphonic acid derivatives of 3-benzylidenecamphor, such as, for example, 4-(2-oxo-3-bornylidenemethyl)benzenesulphonic acid and salts thereof, for example the corresponding sodium, potassium or triethanolammonium salt:

2-methyl-5-(2-oxo-3-bornylidenemethyl)benzenesulphonic acid and salts thereof, for example the corresponding sodium, potassium or triethanolammonium salt:

1,4-di(2-oxo-10-sulpho-3-bornylidenemethyl) benzene and salts thereof (the corresponding 10-sulphato compounds, for example the corresponding sodium, potassium or triethanolammonium salt), also referred to as benzene-1,4-di(2-oxo-3-bornylidenemethyl-10-sulphonic acid:

According to the invention, the electrolyte(s) is/are also advantageously chosen from the group consisting of

(3) aminoacids and salts thereof or anions thereof. Aminoacids are a constituent of the natural moisturizing factor. The addition of aminoacids, in particular of essential aminoacids, is to be regarded as advantageous since moisture can be bound into the skin by hydration processes.

Aminoacids having particularly advantageous cosmetic or dermatological action are glycine, alanine, valine, leucine, isoleucine, phenylalanine, tyrosine, proline, hydroxyproline, serine, threonine, cysteine, methionine, tryptophan and arginine.

According to the invention, the electrolyte(s) is/are also advantageously chosen from the group consisting of (4) the cosmetically and dermatologically relevant α-hydroxycarboxylic acids, α-ketocarboxylic acids and β-hydroxycarboxylic acids and, in particular, the salts thereof, in which case the cations can advantageously be chosen from the group consisting of ammonium, alkylammonium, alkali metal, alkaline earth metal, magnesium, iron and zinc ions.

α-Hydroxycarboxylic acids which are cosmetically or dermatologically relevant conform to the general formula β-Hydroxycarboxylic acids which are cosmetically or dermatologically relevant conform to the general formula α-Ketocarboxylic acids which are cosmetically or dermatologically relevant conform to the general formula in which R' and R'' in each case, independently of one another, are chosen from the group consisting of (a1) H—,
(a2) branched or unbranched $C_{1-25}$-alkyl,
(a3) branched or unbranched $C_{1-25}$-alkyl substituted by one or more carboxyl groups and/or hydroxyl groups and/or aldehyde groups and/or oxo groups (keto groups),
(a4) phenyl,
(a5) phenyl substituted by one or more carboxyl groups and/or hydroxyl groups and/or branched and/or unbranched $C_{1-25}$-alkyl groups, or in which the α-carbon atom and the β-carbon atom of the β-hydroxycarboxylic acid, together with R' and R'', form an
(a6) unsubstituted cycloalkyl group or aryl group having from 3 to 7 ring atoms or a
(a7) cycloalkyl group or aryl group having from 3 to 7 ring atoms and substituted by one or more carboxyl groups and/or hydroxyl groups and/or oxo groups (keto groups) and/or branched and/or unbranched $C_{1-25}$-alkyl groups and in which the α-hydroxycarboxylic acids or the 0-hydroxycarboxylic acids or the β-ketocarboxylic acids may optionally be present in the form of their physiologically tolerated salts.

hydroxycarboxylic acids, β-hydroxycarboxylic acids and α-ketocarboxylic acids which are to be used advantageously are given below, these also being representative of their salts and anions:

Salicylic acid (also 2-hydroxybenzoic acid), which is characterized by the structure

As is known, salicylic acid has an antibacterial and keratolytic effect and is a constituent of some cosmetic or pharmaceutical preparations.

The α-hydroxycarboxylic acids used according to the invention are advantageously chosen from the following classes of substance:

(a2) α-hydroxy fatty acids, these in turn being chosen particularly advantageously from the group consisting of the $C_{10-18}$-alkylcarboxylic acids,
(a3) α-hydroxy sugar acids, aliphatic α-hydroxy fruit acids,
(a4) unsubstituted aromatic α-hydroxycarboxylic acids (e.g. mandelic acid) and
(a5) substituted aromatic α-hydroxycarboxylic acids.

The α-hydroxy fatty acids which fall under point (a2) are particularly advantageously chosen from the group consisting of α-hydroxycarboxylic acids of the formula α-hydroxyisocarboxylic acids of the formula $$CH_3-CH(CH_3)-(CH_2)_n-C(OH)(COOH)-H \quad \text{and/or}$$

α-hydroxyanteisocarboxylic acids of the formula $$CH_3-CH_2-CH(CH_3)-(CH_2)_n-C(OH)(COOH)-H,$$

in which n is in each case a number from 7 to 31.

It is also advantageous to use mixtures of such aliphatic α-hydroxycarboxylic acids, in particular in the form of wool wax acid mixtures, in which the content of α-hydroxycarboxylic acids is 20–30% by weight, based on the total composition.

The α-hydroxy sugar acids which fall under point (a3) are particularly advantageously chosen from the group consisting of aldonic acids, e.g. gluconic acid, galactonic acid aldaric acids, e.g. glucaric acid, galactaric acid (but also the fruit acid tartaric acid, which likewise falls under the definition of aldaric acid)

uronic acids, e.g. glucuronic acid, galacturonic acid glyceric acid.

The aliphatic α-hydroxy fruit acids which fall under point (a3) are particularly advantageously chosen from the group consisting of malic acid, lactic acid, citric acid and tartaric acid.

Malic acid (hydroxysuccinic acid) is characterized by the following chemical structure:

$$HOOC-CH_2-CH(OH)-COOH$$

Lactic acid (2-hydroxypropanoic acid) is characterized by the following chemical structure:

$$CH_3-CH(OH)-COOH$$

Citric acid (2-hydroxypropane-1,2,3-tricarboxylic acid) is characterized by the following structure:

$$HO-C(CH_2-COOH)(CH_2-COOH)-COOH$$

As is known, citric acid is used for buffering cosmetic and/or dermatological preparations, but also as a synergistic substance for antioxidants in skin and hair cosmetics.

Tartaric acid (dihydroxysuccinic acid) is characterized by the following chemical structure:

$$HOOC-CH(OH)-CH(OH)-COOH$$

A preferred α-ketocarboxylic acid is pyruvic acid (α-oxopropanoic acid). It is characterized by the following structure:

$$CH_3-C(=O)-COOH$$

The maximum amount of electrolytes to be used is ultimately dependent on their solubility in the aqueous phase. In principle, however, the teaching according to the invention does not give any maximum amounts as limits since it may even be advantageous in some instances, for whatever reason, to incorporate into a cosmetic or dermatological preparation an additional amount of an electrolyte beyond the solubility of this electrolyte, for example as undissolved solid.

Cosmetic and dermatological preparations according to the invention also advantageously contain inorganic pigments based on metal oxides and/or other metal compounds sparingly water-soluble or water-insoluble, in particular the oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals and mixtures of such oxides. Pigments based on $TiO_2$ are particularly preferred.

For the purposes of the present invention, it is particularly advantageous, although not imperative, if the inorganic pigments are present in hydrophobic form, i.e. they are surface-treated to repel water. This surface treatment can consist in providing the pigments with a thin hydrophobic layer by processes known per se.

One such process consists, for example, in producing the hydrophobic surface layer according to a reaction according to:

$$n\ TiO_2 + m\ (RO)_3\ Si-R' \rightarrow n\ TiO_2\ (\text{surf.})$$

where n and m are arbitrary stoichiometric parameters and R and R' are the desired organic radicals. Pigments rendered hydrophobic as in DE-OS 33 14 742, for example, are advantageous.

Advantageous $TiO_2$ pigments are obtainable, for example, under the tradenames MT 100 T from TAYCA, also M 160 from Kemira and T 805 from Degussa.

The cosmetic and/or dermatological light protection formulations according to the invention can have the conventional compositions and can be used for cosmetic and/or dermatological light protection, and also for the treatment, care and cleansing of the skin and/or hair and as make-up products in decorative cosmetics.

For use, the cosmetic and dermatological preparations according to the invention are applied to the skin and/or hair in sufficient amount and in the manner conventional for cosmetics.

Particularly preferred cosmetic and dermatological preparations are those which are in the form of a sunscreen. Advantageously, these can additionally contain at least one further UVA filter and/or at least one further UVB filter and/or at least one inorganic pigment, preferably an inorganic micropigment.

The cosmetic and dermatological preparations according to the invention can contain cosmetic auxiliaries such as those conventionally used in such preparations, e.g. preservatives, bactericides, perfumes, antifoams, dyes, pigments which have a colouring effect, thickeners, moisturizers and/or humectants, fats, oils, waxes or other conventional constituents of a cosmetic or dermatological formulation, such as alcohols, polyols, polymers, foam stabilizers, electrolytes, organic solvents or silicone derivatives.

An additional content of antioxidants is generally preferred. According to the invention, favourable antioxidants which can be used are any antioxidants suitable or conventional for cosmetic and/or dermatological applications.

The antioxidants are advantageously selected from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, Ψ-lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximines) in very low tolerated doses (e.g. pmol to $\mu$mol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, furfurylidenesorbitol and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin, rutinic acid and derivatives thereof, α-glycosylrutin, ferulic acid, furfurylideneglucitol, carnosine, butylhydroxytoluene, butylhydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active substances which are suitable according to the invention.

The amount of the abovementioned antioxidants (one or more compounds) in the preparations is preferably from 0.001 to 30% by weight, particularly preferably from 0.05 to 20% by weight, especially 1–10% by weight, based on the total weight of the preparation.

If vitamin E and/or derivatives thereof are used as the antioxidant or antioxidants, their respective concentrations are advantageously chosen from the range of 0.001–10% by weight, based on the total weight of the formulation.

If vitamin A or vitamin A derivatives or carotenes or derivatives thereof are used as the antioxidant or antioxidants, their respective concentrations are advantageously chosen from the range of 0.001–10% by weight, based on the total weight of the formulation.

The lipid phase can advantageously be chosen from the following group of substances:

mineral oils, mineral waxes oils, such as triglycerides of capric or caprylic acid, but preferably castor oil;

fats, waxes and other natural and synthetic fatty substances, preferably esters of fatty acids with alcohols having a low number of carbon atoms, e.g. with isopropanol, propylene glycol or glycerol, or esters of fatty alcohols with alkanoic acids having a low number of carbon atoms or with fatty acids;

alkyl benzoates;

silicone oils such as dimethylpolysiloxanes, diethylpolysiloxanes, diphenylpolysiloxanes and mixtures thereof.

For the purposes of the present invention, the oil phase of the emulsions, oleogels and hydrodispersions or lipodispersions is advantageously selected from the group consisting of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group consisting of esters of aromatic carboxylic acids and saturated and/or unsaturated, branched and/or unbranched alcohols having a chain length of from 3 to 30 carbon atoms. Such ester oils can advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semisynthetic and natural mixtures of such esters, e.g. jojoba oil.

The oil phase can also advantageously be selected from the group consisting of branched and unbranched hydrocarbons and hydrocarbon waxes, silicone oils, dialkyl ethers, from the group consisting of saturated or unsaturated, branched or unbranched alcohols, and also fatty acid triglycerides, namely the triglycerol esters of saturated and/or unsaturated, branched and/or unbranched alkanecarboxylic acids having a chain length of from 8 to 24, in particular 12–18, carbon atoms.

The fatty acid triglycerides can advantageously be selected, for example, from the group consisting of synthetic, semisynthetic and natural oils, e.g. olive oil, sunflower oil, soybean oil, peanut oil, rapeseed oil, almond oil, palm oil, coconut oil, palm kernel oil and the like.

For the purposes of the present invention, any mixtures of such oil and wax components can also advantageously be used. When required, it can also be advantageous to use waxes, for example cetyl palmitate, as the only lipid component of the oil phase.

The oil phase is advantageously selected from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicaprylyl ether.

Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous.

For the purposes of the present invention, the hydrocarbons which can advantageously be used are paraffin oil, squalane and squalene.

The oil phase can advantageously also contain cyclic or linear silicone oils or can consist entirely of such oils, although it is preferable to use an additional content of other oil phase components in addition to the silicone oil or silicone oils.

Cyclomethicone (octamethylcyclotetrasiloxane) is advantageously the silicone oil to be used according to the invention. However, other silicone oils can advantageously be used for the purpose of the present invention, for example hexamethylcyclotrisiloxane, polydimethylsiloxane, poly (methylphenylsiloxane).

Mixtures of cyclomethicone and isotridecyl isononanoate and mixtures of cyclomethicone and 2-ethylhexyl isostearate are particularly advantageous.

The aqueous phase of the preparations according to the invention may advantageously contain alcohols, diols or polyols having a low number of carbon atoms, and also their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols having a low number of carbon atoms, e.g. ethanol, isopropanol, 1,2-propanediol, glycerol, and especially one or more thickeners which can advantageously be selected from the group consisting of silicon dioxide, aluminium silicates and polysaccharides and their derivatives, e.g. hyaluronic acid, xanthan gum, hydroxypropylmethylcellulose, and particularly advantageously from the group consisting of polyacrylates, preferably a polyacrylate from the group consisting of the so-called Carbopols, for example Carbopol 980, 981, 1382, 2984, 5984, in each case individually or in combination.

The cosmetic or dermatological light protection preparations advantageously contain inorganic pigments, in particular micropigments, e.g. in amounts of from 0.1% by weight to 30% by weight, preferably in amounts of from 0.5% by weight to 10% by weight, but especially from 1% by weight to 6% by weight, based on the total weight of the preparations.

In addition to the combinations according to the invention, it is advantageous according to the invention to use oil-soluble UVA filters and/or UVB filters in the lipid phase and/or water-soluble UVA filters and/or UVB filters in the aqueous phase.

The light protection formulations according to the invention can advantageously contain further substances which absorb UV radiation in the UVB region, the total amount of filter being e.g. from 0.1% by weight to 30% by weight, preferably from 0.5 to 10% by weight, especially from 1 to 6% by weight, based on the total weight of the preparations, in order to provide cosmetic preparations which protect the skin from the whole region of ultraviolet radiation. They can also be used as sunscreens.

The other UVB filters can be oil-soluble or water-soluble. Examples of advantageous oil-soluble UVB filters are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)-benzoate, amyl 4-(dimethylamino) benzoate;

esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate.

Examples of advantageous water-soluble UVB filters have already been given under advantageous electrolytes according to the invention, but extracts may be listed again here:

salts of 2-phenylbenzimidazole-5-sulphonic acid, such as its sodium, potassium or its triethanolammonium salt, and also the sulphonic acid itself;

sulphonic acid derivatives of benzophenones, preferably 2-hydroxy-4-methoxybenzophenone-5-sulphonic acid and salts thereof;

sulphonic acid derivatives of 3-benzylidenecamphor, such as e.g. 4-(2-oxo-3-bornyli-denemethyl) benzenesulphonic acid, 2-methyl-5-(2-oxo-3-bornylidenemethyl)sulphonic acid and salts thereof.

The list of said further UVB filters, which can be used in combination with the active substance combinations according to the invention, is of course not intended to be limiting.

It can also be advantageous to combine the combinations according to the invention with further UVA filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)-propane-1,3-dione. These combinations and preparations which contain these combinations are also provided by the invention. The amounts which may be used are as for the UVB combination.

It is further advantageous to combine the active substance combinations according to the invention with further UVA and/or UVB filters.

It is also particularly advantageous to combine the active substance combinations according to the invention with salicyclic acid derivatives, some of which, as is known, can also absorb UV radiation. Customary UV filters include (4-isopropylbenzyl salicylate)

(2-ethylhexyl salicylate, octyl salicylate)

(homomenthyl salicylate)

The cosmetic and/or dermatological preparations according to the invention are prepared in the manner known to the person skilled in the art, which in most cases involves suspending and, if desired, homogenizing an oil phase containing interface-active glucose derivatives used according to the invention with uniform stirring and optional heating, optionally combining the mixture with other lipid components and optionally with one or more other emulsifiers, then mixing and, if desired, homogenizing the oil phase with the aqueous phase into which a thickener has optionally been incorporated and which is preferably at about the same temperature as the oil phase, and allowing the mixture to cool to room temperature. After the mixture has cooled to room temperature, homogenization may be repeated, particularly if volatile constituents are still to be incorporated.

The following examples serve to illustrate the present invention, without limiting it. Unless indicated otherwise, all amounts, proportions and percentages are based on the weight and the total amount or on the total weight of the preparations.

EXAMPLE 1

| O/W Lotion | |
|---|---|
| Glyceryl stearate SE | 3.50 |
| Tego Care CG 90 | 1.80 |
| Glycerol | 3.00 |
| Cetearyl alcohol | 0.50 |
| Octyldodecanol | 7.0 |
| Caprylyl ether | 8.0 |
| Eusolex 232 | 3.0 |
| NaOH (45%) | 1.0 |
| Cetearyl isononanoate | 6.0 |
| Carbomer | 0.20 |
| Preservative | q.s. |
| Perfume | q.s. |
| Water, demin. | ad 100.0 |

EXAMPLE 2

| O/W Cream | |
|---|---|
| Glyceryl stearate | 0.50 |
| Tego Care CG 90 | 6.50 |
| Glycerol | 3.00 |
| Cetearyl alcohol | 1.50 |
| Sodium hydroxide (45%) | 1.13 |
| Octyldodecanol | 7.0 |
| Capric/caprylic triglyceride | 5.0 |
| Cetearyl isononanoate | 6.0 |
| Uvinul MS 40 | 3.0 |
| Carbomer | 0.2 |
| Preservative | q.s. |
| Perfume | q.s. |
| Water, demin. | ad 100.0 |

EXAMPLE 3

| O/W Lotion | |
|---|---|
| Tego Care CG 90 | 5.50 |
| Butylene glycol | 5.00 |
| Cetearyl alcohol | 0.50 |
| Xanthan gum | 0.35 |
| $C_{12}$—$C_{15}$ alkyl benzoate | 10.0 |
| Eusolex 232 | 4.0 |

| -continued | |
|---|---|
| O/W Lotion | |
| NaOH (45%) | 1.3 |
| Cetearyl isononanoate | 6.0 |
| Preservative | q.s. |
| Perfume | q.s. |
| Water, demin. | ad 100.0 |

What is claimed is:

1. A cosmetic or dermatologic emulsion comprising:
   a) an oil phase;
   b) one or more aqueous phases;
   c) one or more alkyl glucosides of the formula:

in which R is a branched or unbranched alkyl radical having from 4 to 24 carbon atoms; and $\overline{DP}$ is an average degree of glucosylation of up to 2; and
   d) one or more electrolytes present in dissolved form in at least one of said aqueous phases, the ionic strength of any of said aqueous phases in which any of said electrolytes are present being at least 0.075 ml/l.

2. The emulsion according to claim 1, wherein $\overline{DP}$ ranges from 1–2.

3. The emulsion according to claim 2, wherein $\overline{DP}$ ranges from 1.1–1.5.

4. The emulsion according to claim 3, wherein $\overline{DP}$ is about 1.3.

5. The emulsion according to claim 1, wherein R is selected from the group consisting of unbranched alkyl radicals.

6. The emulsion according to claim 5, wherein R is an unbranched alkyl radical selected from the group consisting of myristyl, cetyl, stearyl and eicosyl radicals.

7. The emulsion according to claim 1, which comprises at least one mixture of stearyl glucoside and cetyl glucoside.

8. The emulsion according to claim 1, which comprises 0.1 to 25.0% by weight of the one or more alkyl glucosides based on the total weight of the emulsion.

9. The emulsion according to claim 8, which comprises 0.5 to 15.0% by weight of the one or more alkyl glucosides based on the total weight of the emulsion.

10. The emulsion according to claim 1, wherein the one or more electrolytes are selected from the group consisting of:
    a) salts comprising anions selected from the chloride anion, inorganic oxo-element anions, and organic anions;
    b) salts comprising cations selected from ammonium, alkylammonium, alkali metal, alkaline earth metal, magnesium, iron and zinc cations;
    c) water-soluble UV filter substances;
    d) amino acids, amino acids salts or anions thereof;
    e) α-hydroxycarboxylic acids, α-ketocarboxylic acids, β-hydroxycarboxylic acids and salts thereof.

11. The emulsion according to claim 10, wherein the one or more electrolytes are selected from the group consisting of:

a) salts comprising an anion selected from chloride, sulfate, carbonate, phosphate, borate, aluminate, lactate, acetate, benzoate, propionate, tartrate, citrate, amino acids, ethylenediaminetetraacetic acid and salts thereof;
b) salts comprising cations selected from ammonium, alkylammonium, alkali metal, alkaline earth metal, magnesium, iron and zinc cations;
c) water-soluble UV filter substances comprising one or more sulphonic acid groups or sulphonate groups;
d) amino acids, amino acids salts or anions thereof;
e) α-hydroxycarboxylic acids, α-ketocarboxylic acids, β-hydroxycarboxylic acids and salts thereof having a cation selected from ammonium, alkylammonium, alkali metal, alkaline earth metal, magnesium, iron and zinc cations.

12. A cosmetic or dermatologic oil-in-water emulsion comprising:
a) an oil phase;
b) one or more aqueous phases;
c) one or more alkyl glucosides of the formula:

in which R is a branched or unbranched alkyl radical having from 4 to 24 carbon atoms; and $\overline{DP}$ is an average degree of glucosylation of up to 2; and
d) one or more electrolytes present in dissolved form in at least one of said aqueous phases, the ionic strength of any of said aqueous phases in which any of said electrolytes are present being at least 0.075 mol/l.

13. The emulsion according to claim 12, wherein $\overline{DP}$ ranges from 1–2.

14. The emulsion according to claim 13, wherein $\overline{DP}$ ranges from 1.1–1.5.

15. The emulsion according to claim 14, wherein $\overline{DP}$ is about 1.3.

16. The emulsion according to claim 12, wherein R is selected from the group consisting of unbranched alkyl radicals.

17. The emulsion according to claim 16, wherein R is an unbranched alkyl radical selected from the group consisting of myristyl, cetyl, stearyl and eicosyl radicals.

18. The emulsion according to claim 12, which comprises at least one mixture of stearyl glucoside and cetyl glucoside.

19. The emulsion according to claim 12, which comprises 0.1 to 25.0% by weight of the one or more alkyl glucosides based on the total weight of the emulsion.

20. The emulsion according to claim 19, which comprises 0.5 to 15.0% by weight of the one or more alkyl glucosides based on the total weight of the emulsion.

21. The emulsion according to claim 12, wherein the one or more electrolytes are selected from the group consisting of:
a) salts comprising anions selected from the chloride anion, inorganic oxo-element anions, and organic anions;
b) salts comprising cations selected from ammonium, alkylammonium, alkali metal, alkaline earth metal, magnesium, iron and zinc cations;
c) water-soluble UV filter substances;
d) amino acids, amino acids salts or anions thereof;
e) α-hydroxycarboxylic acids, α-ketocarboxylic acids, β-hydroxycarboxylic acids and salts thereof.

22. The emulsion according to claim 21, wherein the one or more electrolytes are selected from the group consisting of:
a) salts comprising an anion selected from chloride, sulfate, carbonate, phosphate, borate, aluminate, lactate, acetate, benzoate, propionate, tartrate, citrate, amino acids, ethylenediaminetetraacetic acid and salts thereof;
b) salts comprising cations selected from ammonium, alkylammonium, alkali metal, alkaline earth metal, magnesium, iron and zinc cations;
c) water-soluble UV filter substances comprising one or more sulphonic acid groups or sulphonate groups;
d) amino acids, amino acids salts or anions thereof,
e) α-hydroxycarboxylic acids, α-ketocarboxylic acids, β-hydroxycarboxylic acids and salts thereof having a cation selected from ammonium, alkylammonium, alkali metal, alkaline earth metal, magnesium, iron and zinc cations.

23. A method of caring for skin comprising topically applying thereto an effective amount therefor of an emulsion according to any one of claims 1–22.

* * * * *